United States Patent [19]

Kirkwood et al.

[11] Patent Number: 4,617,272

[45] Date of Patent: Oct. 14, 1986

[54] ENZYME DRYING PROCESS

[75] Inventors: Marda K. Kirkwood, White Bear Lake; Keith E. Olson, Apple Valley, both of Minn.

[73] Assignee: Economics Laboratory, Inc., St. Paul, Minn.

[21] Appl. No.: 603,711

[22] Filed: Apr. 25, 1984

[51] Int. Cl.$^4$ .............................................. C12N 9/00
[52] U.S. Cl. ...................................... 435/183; 435/803; 435/814; 159/3; 159/48.1; 426/471; 426/472
[58] Field of Search ................... 159/3, 48.1; 435/195, 435/312, 313, 315, 316, 183, 814; 426/471, 472, 492

[56] References Cited

U.S. PATENT DOCUMENTS

| | | | |
|---|---|---|---|
| 3,676,064 | 7/1972 | Shick | 159/3 X |
| 3,676,352 | 7/1972 | Grimm et al. | 252/99 |
| 3,687,717 | 8/1972 | Philip | 117/100 A |
| 3,746,621 | 7/1973 | Kondo et al. | 195/63 |
| 3,773,623 | 11/1973 | Hatcher et al. | 195/60 |
| 4,281,024 | 7/1981 | Hauberg et al. | 426/471 |
| 4,298,339 | 11/1981 | Randell | 159/48.1 |
| 4,352,718 | 10/1982 | Grün | 159/48 R |
| 4,490,403 | 12/1984 | Pisecky et al. | 426/471 |

FOREIGN PATENT DOCUMENTS

| | | | |
|---|---|---|---|
| 0005072 | 1/1978 | Japan | 159/3 |
| 1151748 | 5/1969 | United Kingdom . | |

OTHER PUBLICATIONS

Sigma Chemical Catalog Price List, Feb. 1982, p. 463.

*Primary Examiner*—Christine M. Nucker
*Assistant Examiner*—Stephen C. Wieder
*Attorney, Agent, or Firm*—Merchant, Gould, Smith, Edell, Welter & Schmidt

[57] ABSTRACT

A process for removing the water from an enzyme-containing aqueous medium is disclosed which comprises spraying the medium onto a heated, fluidized bed of inert substrate particles and recovering a dry enzyme concentrate therefrom.

14 Claims, 1 Drawing Figure

ENZYME DRYING PROCESS

FIELD OF THE INVENTION

The present invention relates to methods for drying aqueous media containing enzymes or other biologically-active substances by a fluidized bed technique which leads to isolated enzymes with substantially-retained biochemical activity.

BACKGROUND OF THE INVENTION

Enzymes are proteins which catalyze a wide variety of chemical reactions, many of great commercial importance. Many enzymes are produced by culturing specific strains of molds, yeast or bacteria. The microbiological synthesis of enzymes is increasing in importance due to the fact the fermentation times are short, the growth media are inexpensive, and simple screening procedures of enzymatic activity have been developed. Typically, an enzyme-producing microorganism is grown under controlled conditions in an aqueous medium containing nutrients, buffers and the like. The growth of the microorganism may be terminated, which "stops" the production of enzyme, and the enzyme is then stabilized, for example, by the addition of chemicals such as polyethylene glycols. However, even in the presence of stabilizers, enzymatic activity often decreases in aqueous media. Therefore, such enzyme-containing solutions must either be shipped and used soon after receipt, or the enzymes must be isolated in the dry state.

Dry enzyme concentrates are desirable for a number of reasons: (a) their activity remains substantially constant for an indefinite period of time under ambient conditions; (b) due to their high activity per unit weight, they are much more economical to store and ship than are aqueous solutions; and (c) they can be readily redissolved to form solutions of varying, precisely-controlled activities.

The advantages of dry enzyme preparations have encouraged the development of methods to remove the large excesses of water from the relatively minor amounts of active solids which are dissolved or suspended therein. However, all of the currently available methods suffer from a number of significant disadvantages. Lyophilization preserves enzymatic activity but is extremely energy intensive due to the need to maintain high vacuums for long periods of time. Chemical precipitation requires expensive additives and often requires further purification steps to remove them after the residue has been isolated. Effective spray-drying requires either tower temperatures which lead to unacceptable enzyme deactivation or expensive enzyme recycling mechanisms.

Therefore, methods are needed for drying aqueous solutions of enzymes which allow substantial enzymatic activity to be retained in the dried products. A useful method should produce dry enzyme concentrates rapidly and employ moderate processing conditions.

BRIEF DESCRIPTION OF THE INVENTION

The present invention is directed to a process comprising contacting (e.g. by spraying) an aqueous enzyme-containing medium with a heated, fluidized bed comprising an inert particulate substrate. The heat and action of the bed dries the aqueous medium, resulting in a dried product. Although a minor portion of the medium will be dried solely by the hot fluidizing gas stream, a major portion of the enzyme-containing medium forms a thin film on the moving substrate which rapidly dries, depositing a layer or crust of enzyme-containing powder. During the drying process, this crust is at least partially released from the substrate surface by the abrasive action of adjacent particles. A part of the resultant free powder product remains entrained in the bed, while a part is separated therefrom by the gas stream used to fluidize the bed, from which it may be removed by conventional techniques. The powder remaining in the bed may be separated from the substrate, e.g. by screening and the powder remaining adhered to the substrate may also be readily recovered.

Since the present method comprises contacting fine droplets of the enzyme-containing medium with a moving bed of substrate particles possessing a large effective surface area, evaporation of the water by the fluidizing gas stream is extremely rapid, thus permitting the use of solution and bed temperatures as well as drying times, which do not result in significant enzyme deactivation. The use of chemically-inert substrate particles and the ability of the present method to function effectively in the absence of conventional stabilizers allows the preparation of dry enzyme concentrates as free-flowing powders from dilute aqueous media with the retention of a substantial percentage of the total enzymatic activity initially present.

The term "dry" or "water-free" as used herein with respect to the enzyme concentrates produced by the present invention is intended to refer to enzyme concentrates which comprise water in amounts which do not substantially effect the stability of the activity of said concentrates under ambient temperatures (18°–25° C.). The concentrates produced by the present methods are generally dry, free-flowing powders having particles diameters within the range of about 1 mm–1 micron.

The term "aqueous medium or media" is intended to refer to the aqueous solutions or suspensions which can contain a variety of additives such as nutrients, buffers, and nonaqueous liquids, and which can be processed by the present invention.

DETAILED DESCRIPTION OF THE PRESENT INVENTION

Enzyme Preparations

Figure 1:
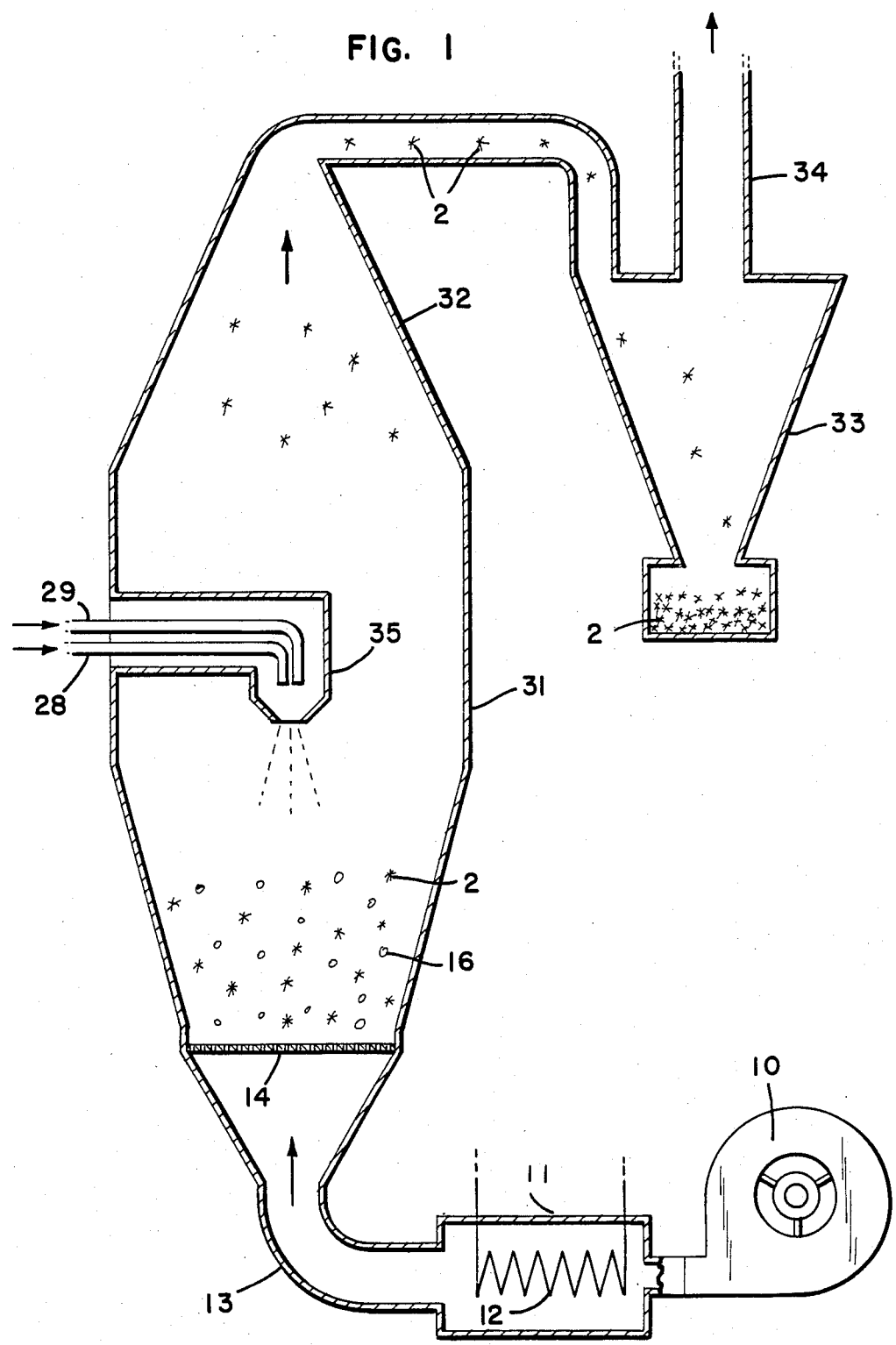

The spray fluidization drying method described herein is useful to remove substantially all of the water from an aqueous enzyme-containing medium, thus permitting the recovery of a powdered enzyme concentrate which also may comprise minor amounts of solid nutrients, stabilizers, stopping agents and the like. The enzyme-containing concentrates can be recovered under processing conditions which allow the retention of at least 50%, preferably at least 60% and most preferably about 70–100% of the total enzymatic activity present in the aqueous medium processed. The percent retention of enzymatic activity of a powdered concentrate recovered by the methods of the present invention is determined according to the following formula:

$$\text{Percent Retention} = \frac{[\text{Activity of dry powder } (U/g) \times \text{Solution density } (g/ml)]}{\text{Activity of liquid medium } (U/ml) \times (\text{Wt. \% solids in medium})}$$

Enzymatic activity of a solution or solid is typically expressed in U(units)/weight or volume unit of the solution or solid. Units of activity are determined by standardized test methods which are specific to a given enzyme or class of enzymes, and which are designed to measure the ability of the enzyme to interact with a specific substrate.

The activity of the great majority of useful enzymes rapidly decreases in aqueous media, a phenomenon which is probably due in part to the presence of proteolytic enzymes which indiscriminately degrade any protein present. Exponential rates of decay have been observed for some species. The instability of aqueous enzyme-containing media has presented many difficulties in shipping and storing such media in situations where solutions of standardized activity are required. The aqueous enzyme product often must be used soon after preparation to insure that adequate activity will be present to accomplish the intended transformation.

Since many dry enzyme preparations have been found to possess activities which are essentially stable, the present process is designed to effect the removal of the water from aqueous enzyme-containing media without substantially degrading the total enzymatic activity of the medium during the processing steps. The present process can be adapted to dry aqueous media comprising a broad spectrum of useful enzymes, including but not limited to the commercially-cultured lipase, protease, glucamylase, amylase and glucose isomerase enzymes. The amylases are a family of enzymes that break down starch first into short chains by glucose molecules and then into free glucose. Glucose isomerase converts glucose into its stereoisomer fructose, a useful food sweetener. A combination of alphaamylase, glucamylase and glucose isomerase is used to produce high-fructose syrups from cornstarch. Amylases are also used in brewing, baking and the manufacture of textiles. Pectinase enzymes derived from molds are useful in fruit processing while mold-drived microbial rennet is employed in the cheese industry. Other useful enzymes include those employed to effect genetic manipulations such as RNAase, DNAase, ligases and restriction endonucleases.

The present method is particularly well-adapted to produce powdered concentrates of hydrolytic enzymes, such as protease enzymes. Protease actually encompasses several enzymes that degrade proteins by attacking peptide bonds. The main industrial protease, obtained from the bacterium *Bacillus licheniformis*, serves mainly as a cleaning aid in detergents. Proteases from other bacteria and fungi are employed as digestive aids in animal feed, in meat tenderizers, in leather manufacture and in other processes where the total or partial degradation of protein is desired. For a thorough discussion of protease enzymes useful to attack soil in laundering operations, see British Pat. No. 1,151,748, the disclosure of which is incorporated by reference herein.

Levan Hydrolase

The hydrolase enzyme selected for use in the process as exemplified herein is levan hydrolase which is available from Economics Laboratory, Inc., St. Paul, MN. This enzyme, hereinafter designated as EDC-1, is presently used in aqueous solution to prevent the accumulation of slime in paper manufacturing equipment and is described in U.S. Pat. Nos. 3,773,623 and 3,824,184, the disclosures of which are incorporated by reference herein. Heretofore, the enzyme has been provided in aqueous media incorporating about 1.0–15% total solids, preferably about 2.0–10%, and exhibiting an initial activity of about 500–3000 U/ml, preferably about 800–2000 U/ml. After stopping, the activity of this enzyme rapidly decays at room temperature, i.e. about 25% of the initial activity is lost after about 40 hours at 25° C. The activity of aqueous solutions of EDC-1 or of the dried concentrates derived therefrom is determined by the following method:

A 1:10 dilution of an EDC-1 concentrate in water is prepared. A 1 ml portion of the diluted enzyme is mixed with 2.0 ml of 0.05M citrate buffer and equilibrated to 122° F. Leven substrate for the assay was prepared using *Aerobacter levanicum* according to the method of L. Avigad as set forth in *Methods of Carbohydrate Chemistry V*, Academic Press, New York (1965) at pages 161–165, and 2.0 ml of a 4.5% w/v mixture of the substrate in water is added to the enzyme-containing tube. After 10 minutes, a 1.0 ml portion of the reaction mixture was added to a tube containing 3.0 ml of 2% NaOH and 1.0 ml of 2% Tetrazolium Blue (BT, ICN Pharmaceuticals, Cleveland, OH). After 5 minutes, 5.0 ml of a 25% phosphoric acid solution was added to the Tetrazolium Blue tube and the percent transmittance at 595 nm determined with a colorimeter vs. a thermally deactivated portion of the diluted enzyme which was similarly treated for use as the spectrometric blank. The enzymatic activity is calculated using the following formula:

$$\text{Activity (U/ml)} = (100 - \%T)/0.1$$

According to the method of the present invention, aqueous enzyme-containing media are dried by spraying them onto a heated, fluidized bed of a suitable particulate substrate. Droplets of media can form a coating on the warm substrate which rapidly dries by evaporation to provide a dry powder comprising the enzyme.

Bed Substrates

Substrates useful in the practice of the present invention include particles of an inert material, i.e. a material which does not chemically bond to or otherwise interact with the enzyme. The inert material is preferably a plastic material such as a natural or synthetic polymer. Useful polymers include those selected from the group consisting of colored or uncolored resins such as polyethylene, polypropylene, polyethylene terephthalate, polymethylmethacrylate, polystyrene, polycarbonate, a fluoropolymer (e.g., Teflon®) and mixtures thereof. The substrate must be selected so as to resist substantial absorption of the medium, but, on the other hand, must be sufficiently resilient to resist chipping or fragmenting in the moving bed. The particles may be spherical, cubic, cylindrical or of random shapes. Rounded, substantially spherical particles are preferred due to their tendency to resist fragmentation when fluidized and agglomeration when sprayed. Preferably, the spherical particles will possess a diameter within the range of about 0.06–0.15 inches. Especially preferred particles for use as substrates in the present fluidized beds include colored or uncolored beads of polytetrafluoroethylene, tetrafluoroethylene-hexafluoropropylene copolymer, polyethylene, ethylene-hexene copolymer and polypropylene.

Bed Fluidization

The particulate beds are fluidized and heated by a stream of gas. Air is the preferred fluidizing gas but inert gasses such as argon, nitrogen and the like may be employed if the exclusion of oxygen from the drying apparatus is desired. The temperature of the fluidizing gas is selected so as to maintain the static or continuously-renewed fluidized bed at a temperature adequate to dry the wetted particles without increasing their temperature above the point where substantial enzymatic activity is lost. Although useful bed temperatures will vary depending on the temperature sensitivity of the enzyme dried thereon, bed temperatures useful to dry a wide variety of enzymes are found to fall within the range of about 100°–180° F., preferably about 110°–140° F. The fluidizing gas inlet temperatures required to maintain these ranges will vary depending on the weight of the water which is to be removed and the bed renewal rate, if any, but typically will be 120° F. or more, e.g. about 120°–500° F., preferably about 120°–300° F.

Aqueous Media

In order to minimize loss of enzymatic activity, the enzyme-containing medium is maintained at less than about 100° F. prior to spraying, preferably at about 45°–75° F. Cooling the medium below about 40° F. and/or adding commonly-employed enzyme stabilizers such as calcium acetate and polyethylene glycol does not significantly effect activity retention. It was found desirable to avoid the use of stabilizers other than the sodium sulfite preservative, since they caused increased powder adherence and agglomeration, thus inhibiting release of the dried powder from the beads and its subsequent redissolution.

A stream of the 40°–100° F. medium is contacted with the bed particles, preferably after having been atomized, as in a two-fluid nozzle wherein the atomizing air stream may be optionally heated to about 150°–200° F. and pressurized at about 14–30 psig, or in a pressure nozzle operated at pressures of up to about 100 psig.

The liquid spray rate will be set so as to maintain the bed temperature within the preferred range. For any given air inlet temperature, an increase in spray rate will lower the bed temperature, eventually causing bed collapse due to agglomeration of the moist bed particles.

Adherence

When the spray of enzyme-containing medium contacts the heated bed particles, it can coat the particle surface with a liquid film which can rapidly evaporate in the fluidizing gas stream to deposit a dry powder comprising the enzyme. In the practice of the present process, a part of the dried powder is removed from the particles by the friction generated as they collide in the bed. A portion of this powder remains comingled with the beads while a portion is removed from the bed by the fluidizing gas stream. Both the portion which is removed by the gas stream and the portion which is admixed with the bed particles is easily recovered by standard techniques. The powder entrained in the fluidizing gas stream may be recovered by a suitable filter or cyclone-type collector, while the powder comingled with the bed particles may be isolated by passing the bed through a sieve sized so as to retain the bed particles.

The amount of dried enzyme concentrate which remains attached to the bed particles (beads) is quantated as Percent Adherence by the formula:

$$\text{Percent Adherence} = \frac{\left(\begin{array}{c}\text{wt. of beads}\\\text{after drying}\end{array}\right) - \left(\begin{array}{c}\text{wt. of beads}\\\text{before drying}\end{array}\right)}{\left(\begin{array}{c}\text{wt. of liquid}\\\text{sprayed}\end{array}\right) \times \left(\frac{\text{wt. \% non-volatiles}}{100}\right)} \times 100$$

In some cases, the bed substrate and conditions required to effectively dry a given enzyme will result in the adherence of a major amount of the enzyme concentrate to the substrate at the completion of the drying process. However, even adherence levels of 80–100% do not substantially reduce the utility of the present process, since the adhered enzyme concentrate can be readily recovered from the beads, i.e. by conventional frictional, compressional or ultrasonic techniques. Such techniques include separating the beads from the finer free enzyme powder by isolating the beads on an suitably-sized screen, compressing the beads in a roller mill to loosen the adhered enzyme powder, followed by a second screening step to isolate the beads for recycling. However, in other cases, drying parameters will be selected which result in adherence values of less than about 50%, e.g. as low as 0–20%. At an adherence value of less than 50%, the major amount of the dried enzyme concentrate coating is released from the substrate particles during the course of the drying process, and remains mixed with the bed particles or is recovered from the fluidizing gas stream via filters and/or dust collectors and the like.

Continuous Bed Renewal

Although fluidized beds which are otherwise static are effective to dry relatively small amounts of aqueous media, for optimal drying efficiency the fluidized bed is preferably stirred or shaken during the drying process so as to more rapidly and evenly coat the total substrate surface with the impinging spray. In addition to in situ agitation of the bed, the bed of substrate particles is preferably renewed in a continuous fashion, whereby uncoated particles are continuously introduced into the spray area of the fluidized bed while a substantially equal portion of sprayed, preferably dry particles are removed from the bed. The use in the present process of a continuously-renewed bed increases the effective particle surface area to which the aqueous medium is exposed, thus greatly increasing the efficiency of the drying process. In practice, the sprayed particles can optionally be moved over a perforated plate where they are maintained as a heated, fluidized bed but not further sprayed. This additional exposure to the fluidizing gas stream can help to complete the drying process and removes a higher proportion of the adhered enzyme coating.

Since the beads can be recycled once they have been stripped of any adhered solids, the cost of the additional beads is not a limiting factor when selecting the bead flow-through rate. Rather, the upper limits of this parameter are fixed only by the requirement that the sprayed particles removed from the bed be adequately dried during their residence time in the bed. For example, bead flow-through rates of about 0.1–10 lbs/min./ft² of sprayed bed, preferably about 1-7 lbs/min./ft² of sprayed bed have been found to effectively increase the drying rate.

As recovered, the enzyme concentrate is a dry, free-flowing powder which redissolves readily in water and is substantially free of agglomerated particles by visual observation. The enzymatic activity is stable indefinitely under ambient conditions, thus permitting the dried enzyme to be shipped, stored and reconstituted in situ for its end use application.

Although the process of the present invention has been exemplified by its use to produce a dry enzyme concentrate, it is expected that it will effectively dry aqueous solutions or suspensions comprising a wide variety of water- and/or thermally-unstable materials, including antibodies, antigens, microorganisms, antibiotics, hormones and the like.

The invention will be further described by reference to the following detailed examples.

EXAMPLE I

There will now be described the application of the invention on the bench scale to the production of a dry, free-flowing enzyme powder (*,2) from an aqueous enzyme-containing solution. A form of apparatus suitable for use in the method is illustrated in FIG. 1, which is a diagrammatic vertical section.

The apparatus comprises a generally conical casing 31, having at its lower end an inlet duct 13 for the fluidizing gas which is compressed by pump 10 and heated in chamber 11 by heating element 12. At its upper end, casing 31 has an outlet exhaust hood 32 which communicates with duct collector 33. The dust-free gas exits via outlet 34. The floor of the casing 31 is constituted by an air-permeable bed support member, 14, which may be a perforated plate, a screen or the like. In larger scale, i.e. pilot plant units, support 14 may be movably mounted and agitated during the drying process, as by a vibrator (not shown). The openings in support 14 are sized as to retain a bed of particulate substrate 16.

The casing 31 also has a two-fluid spray nozzle 35 attached to its upper inside surface connected to a valve-operated line 28 for the supply of the liquid enzyme medium, which is pumped from a suitable reservoir (not shown); and a line 29 to supply compressed air to atomize the aqueous medium as it issues from the spray head 35. The nozzle air supply may be preheated, i.e. by an in-line electrical heater (not shown).

A 1 Kg. batch, fluidized bed drier of the design depicted in FIG. 1 is commercially available as the STREA-1 model from Aeromatic Co. (Towaco, NJ).

In one run carried out using the 1 Kg. batch fluidized bed STREA-1 apparatus, the bed was loaded with 300 g of polypropylene beads (Northern Petrochemical Co., NPP 8420 HK). The nozzle atomization air was maintained within a temperature range of 150°-200° F. (14.5-29.0 psi pressure) during the run. The fluidization inlet air was maintained at 172°-183° F. During the 3 hour 13 minute run, the exhaust air temperature, which was assumed to be about equal to the temperature of the bed, varied from 115°-127° F. A total of 803 grams of an aqueous solution of EDC-1 (4.37% solids, 900 U/ml, 1.5% sodium sulfite) was dried, which was drawn from a reservoir maintained at 44°-69° F. A gravity dust collector was constructed by running the exhaust gas stream into the bottom of a 41 gallon fiber drum.

After all of the enzyme-containing solution had been sprayed, the bed contents were removed from the casing, weighed, and screened to isolate the loose enzyme powder. The recovered enzyme powder was combined with the dry enzyme powder recovered from the dust collector. The powder readily dissolved in water. No clumping or agglomeration was observed. The retention of activity was colorimetrically determined to be 82%. The percent adherence was determined to be 22%.

TABLE I summarizes four additional runs conducted to dry enzyme EDC-1 solutions which were carried out following the procedure of Example I.

TABLE I

BENCH SCALE RUNS

| PARAMETERS | EXAMPLES | | | |
|---|---|---|---|---|
| | II | III | IV | V |
| Enzyme Solution | | | | |
| Percent Solids | 5.05 | 14.2 | 4.69 | 4.37 |
| Activity (U/ml) | 1130 | 1020 | 1120 | 780 |
| Stabilizer | 1.5% Na₂SO₃ | 1.5% Na₂SO₃ + 10% PEG+ | 1.5% Na₂SO₃ | 1.5% Na₂SO₃ |
| Temperature | 64-68° F. | 61-72° F. | 46-64° F. | 48-64° F. |
| Drier | | | | |
| Bead | Teflon* | Colored Polyethylene (CP)** | CP | Polypropylene*** |
| Inlet Air Temperature | 144-160° F. | 140-145° F. | 167-183° F. | 154-174° F. |
| Exhaust Air Temperature (est. bed temp.) | 110-124° F. | 110° F. est. | 117-130° F. | 119-127° F. |
| Free Powder Collection | Cyclone | Screen | Cyclone | Cyclone |
| Dried Enzyme | | | | |
| Activity (U/g) | 18,400 | 5,700 | 17,000 | 14,400 |
| Retention (%) | 82 | 79 | 71 | 81 |
| Adherence (%) | 11 | 25 | 22 | 24 |
| Redissolves Easily | Yes | Yes | Yes | Yes |

TABLE I-continued

BENCH SCALE RUNS

| PARAMETERS | EXAMPLES | | | |
|---|---|---|---|---|
| | II | III | IV | V |
| Agglomeration | No | No | No | No |

*Teflon ® FEP 140 - Tetrafluoroethylene/hexafluoropropylene copolymer, E. I. duPont, Wilmington, DE.
**Marlex HMN 4550 - High density Ethylene Hexene Copolymer; Phillips Petroleum Co., Bartlesville, OK; 0.94 g/cc; Melt Flow Rate 5 g/10 min.; Tensile strength 3500 psi; Color: PMS Consolidated 030597 CMB turquoise.
***Northern Petrochemical Co., NPP8420 HK; Density 0.9 g/cc; Melt Flow Rate 6 g/10 min.; Tensile strength 4000 psi.
+PEG = Polyethylene glycol of molecular weight of about 8000.

The data summarized in TABLE I demonstrates that the method of the present invention effectively dries enzyme-containing solutions to yield free-flowing enzyme powders which possess a high retention of activity and redissolve easily without agglomeration.

EXAMPLE VI

TABLE II summarizes the results attained when the procedures and apparatus described in Examples I-V were adapted to dry the aqueous enzyme-containing media on the pilot plant scale.

These runs employed 0.125 inch polypropylene beads which were recycled continuously during the drying run. A stream of these beads was continuously fed onto a vibrating 3.0'×5.0' (w×1) perforated plate (Barr and Murphy Intl., Ltd. Vibrator Fluidized Bed, London, UK) and fluidized with a 248°-251° F. inlet air stream. The bed depth in this section was maintained at 6.0 inches. A 5.2% solids solution of EDC-1 enzyme (1.5% sodium sulfate) exhibiting a pre-spray activity of 1020 U/ml was atomized by unheated air (20 psig) and sprayed onto the moving bed at the rate indicated. Although the bed temperature was not directly measured in this system it was thought to be slightly higher than the exhaust duct temperature in each instance, i.e. about 115°-120° F. After passing over the bed at 10-40 lb/min, the bed passed out of the spray area and over a 3.0'×12.0' perforated plate where the fluidizing air temperature was 150° F. and then over a 3.0'×5.0' plate where the fluidizing air was unheated. The beads were then passed out of the fluidizing chamber and over a screen to collect the entrained enzyme powder which had not been carried into the cyclone collector by the exhausted fluidizing air. The bead stream was then reintroduced into the sprayed bed area.

TABLE II

CONTINUOUS BED DRYING

| PARAMETERS | EXAMPLES | | |
|---|---|---|---|
| | A | B | C |
| Enzyme Soln. Temp. | 64° F. | 66-67° F. | 72° F. |
| Pump Rate (gal/min) | 0.56 | 0.73 | 0.58 |
| Total Soln. Sprayed | 485 lbs. | 640 lbs. | 665 lbs. |
| Exhaust Duct Temp. | 108° F. | 111° F. | 117° F. |
| Bead Feed Rate | 10 lb/min. | 20 lb/min. | 40 lb/min. |
| Total Run Time | 3.0 hrs. | 1.75 hrs. | 3.0 hrs. |
| Solids Activity (U/g) | 12,000 | 12,400 | 12,400 |
| Retention (%)* | 61 | 63 | 63 |
| Adherence (%) | 54 | 54 | 27 |
| Redissolves Easily | Yes | Yes | Yes |
| Agglomeration | No | No | No |

*Dust collected in cyclone; dust adhered to beads retained 39% activity at the end of the run.

The results summarized on Table II demonstrate the feasibility of continuous pilot-plant scale enzyme drying utilizing the general feature of the static bench-scale process. The free enzyme powder which was collected exhibited an acceptably-high retention of activity and readily redissolved without observed agglomerated particles.

Although, due to exposure to repeated heating cycles, the activity of the adhered enzyme was substantially less than that of the enzyme powder collected via the cyclone collector or separated by the screening process, it is expected that the overall efficiency of the continuous process can be improved by substantially complete removal of the adhered enzyme from the beads after they leave the bed. This dried enzyme is readily removable by conventional means, i.e. by roller milling and screening.

The invention has been described with reference to various specific and preferred embodiments and techniques. However, it should be understood that many variations and modifications may be made while remaining within the spirit and scope of the invention.

We claim:

1. A process for removing the water from an enzyme-containing aqueous medium comprising:
    forming a heated fluidized bed of inert particles by means of a gas stream wherein said fluidized bed is maintained at about 100°-180° F.
    contacting said heated inert particles with a spray of an enzyme containing medium, wherein said medium is sprayed at a temperature at about 40°-100° F. resulting in the evaporation of the water and the deposition on said inert particles of a dry powder comprising said enzyme; and
    separating said dry enzyme-containing powder from said particles.

2. The process of claim 1 further comprising continuously introducing inert particles into said fluidized bed while removing a substantially equal number of sprayed particles from said bed.

3. The process of claim 1 wherein the particles are spheres formed from a plastic polymer.

4. The process of claim 3 wherein the polymer is selected from the group consisting of polyethylene, polypropylene, polystyrene, polycarbonate, a fluoropolymer and mixtures thereof.

5. The process of claim 1 wherein a major amount of said dry powder remains adhered to said particles prior to the separation step.

6. The process of claim 1 wherein a major amount of said dry powder is released from said particles prior to the separation step.

7. The process of claim 1 wherein the dry powder is separated from the particles by frictional, compressional or ultrasonic techniques.

8. The process of claim 7 wherein the compressional technique comprises compressing the particles in a roller mill.

9. The process of claim 1 wherein the enzyme is a hydrolytic enzyme.

10. The process of claim 9 wherein the enzyme is levan hydrolase enzyme.

11. The process of claim 1 wherein the enzyme powder retains at least about 50% of the total enzymatic activity of the aqueous medium and is not agglomerated.

12. A process for removing the water from an aqueous medium containing a protease enzyme comprising:

forming a fluidized bed of polypropylene beads heated to about 110°-140° F. by means of an air stream;

contacting said heated beads with an about 45°-75° F. spray of an enzyme containing medium resulting in the evaporation of the water and the deposition on the particles of a dry powder comprising said enzyme; and separating said dry enzyme-containing powder from said particles, wherein said dry powder retains at least about 60% of the initial enzymatic activity of the medium.

13. The process of claim 12 wherein the bed is agitated and is continuously renewed by introducing inert particles into said fluidized bed while removing substantially equal numbers of sprayed particles from said bed.

14. The process of claim 12 wherein the enzyme is levan hydrolase enzyme.

* * * * *

UNITED STATES PATENT AND TRADEMARK OFFICE
CERTIFICATE OF CORRECTION

PATENT NO. : 4,617,272
DATED : October 14, 1986
INVENTOR(S) : Marda K. Kirkwood and Keith E. Olson It is certified that error appears in the above-identified patent and that said Letters Patent is hereby corrected as shown below:

Column 3, line 39, "mold-drived" should read --mold-derived--.

Column 4, line 29, "spectrometric" should read --spectrophotometric--.

Column 7, line 33, "with duct collector 33." should read --with dust collector 33.--.

Column 9, line 66, "the general feature of" should read --the general features of--.

Column 12, line 7, "of the medium." should read --of the medium and is not agglomerated.--.

Signed and Sealed this

Thirtieth Day of December, 1986

*Attest:*

DONALD J. QUIGG

*Attesting Officer*  *Commissioner of Patents and Trademarks*